US012702382B2

(12) United States Patent
Igarashi et al.

(10) Patent No.: US 12,702,382 B2
(45) Date of Patent: Aug. 11, 2026

(54) MEDICAL IMAGE PROCESSING DEVICE AND COMPUTER PROGRAM PRODUCT

(71) Applicant: Canon Kabushiki Kaisha, Tokyo (JP)

(72) Inventors: Yu Igarashi, Utsunomiya (JP); Masaki Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/514,415

(22) Filed: Oct. 29, 2021

(65) Prior Publication Data

US 2022/0133276 A1 May 5, 2022

(30) Foreign Application Priority Data

Nov. 5, 2020 (JP) ................................. 2020-185354

(51) Int. Cl.

*A61B 8/00* (2006.01)
*A61B 8/06* (2006.01)
*G06T 7/246* (2017.01)
*G06V 10/25* (2022.01)

(52) U.S. Cl.

CPC .............. *A61B 8/481* (2013.01); *A61B 8/463* (2013.01); *A61B 8/469* (2013.01); *A61B 8/5223* (2013.01); *A61B 8/5246* (2013.01); *G06T 7/246* (2017.01); *G06V 10/25* (2022.01); *A61B 8/06* (2013.01);

(Continued)

(58) Field of Classification Search

CPC ......... A61B 8/481; A61B 8/463; A61B 8/469; A61B 8/5223; A61B 8/5246; A61B 8/06; A61B 8/0891; A61B 8/08; A61B 8/085; A61B 8/48; A61B 8/488; A61B 8/5207; A61B 8/5215; G06T 7/246; G06T 2207/10016; G06T 2207/10132; G06T 5/007; G06T 5/20; G06T 7/0012; G06T 7/62; G06T 7/73; G06V 10/25

See application file for complete search history.

(56) References Cited

U.S. PATENT DOCUMENTS 6,309,353 B1 10/2001 Cheng et al.
7,022,079 B2 4/2006 Ogasawara
9,928,593 B2 3/2018 Ooga et al.

(Continued)

FOREIGN PATENT DOCUMENTS

CN 102246207 A 11/2011
CN 102247144 A 11/2011

(Continued)

OTHER PUBLICATIONS

Combined Chinese Office Action and Search Report issued Jun. 29, 2023 in Chinese Application 202111303312.6, 10 pages.

(Continued)

*Primary Examiner* — Jonathan Cwern
(74) *Attorney, Agent, or Firm* — Oblon, McClelland, Maier & Neustadt, L.L.P.

(57) ABSTRACT

A medical image processing device according to an embodiment includes processing circuitry. The processing circuitry detects a contrast medium from a medical image. The processing circuitry sets a first region of interest and a second region of interest in the medical image. The processing circuitry calculates a density ratio between a density of the contrast medium included in the first region of interest and a density of the contrast medium included in the second region of interest.

18 Claims, 9 Drawing Sheets

(52) U.S. Cl.
CPC ............... *G06T 2207/10016* (2013.01); *G06T 2207/10132* (2013.01)

(56) References Cited

U.S. PATENT DOCUMENTS

| | | | |
|---|---|---|---|
| 10,249,043 B2 | 4/2019 | Ooga et al. | |
| 2004/0159155 A1 | 8/2004 | Ogasawara | |
| 2005/0267371 A1 | 12/2005 | Ogasawara | |
| 2009/0016586 A1 | 1/2009 | Gardner et al. | |
| 2013/0261445 A1* | 10/2013 | Ertel | A61B 5/72 600/431 |
| 2014/0121513 A1* | 5/2014 | Tolkowsky | G06T 7/20 600/431 |
| 2015/0262358 A1* | 9/2015 | Schormans | G06T 7/0016 382/103 |
| 2015/0356734 A1 | 12/2015 | Ooga et al. | |
| 2018/0174297 A1 | 6/2018 | Ooga et al. | |
| 2019/0038239 A1* | 2/2019 | Flohr | A61B 8/5223 |
| 2019/0298304 A1 | 10/2019 | Igarashi et al. | |
| 2020/0234442 A1* | 7/2020 | Barnes | C12Q 1/6886 |
| 2022/0240899 A1* | 8/2022 | Trzasko | G01S 7/52036 |

FOREIGN PATENT DOCUMENTS

| | | |
|---|---|---|
| CN | 110313943 A | 10/2019 |
| JP | 2000-126182 A | 5/2000 |
| JP | 2003-061959 A | 3/2003 |
| JP | 2005-095376 A | 4/2005 |
| JP | 2014-113264 A | 6/2014 |
| JP | 2015-029811 A | 2/2015 |
| JP | 2018-15155 A | 2/2018 |
| JP | 2019-181183 A | 10/2019 |

OTHER PUBLICATIONS

Notice of Reasons for Refusal issued May 29, 2024, in corresponding Japanese Patent Application No. 2020-185354, 6 pages.

Japanese Office Action issued Mar. 18, 2026 in Japanese Patent Application No. 2025-112395, 4 pgs.

* cited by examiner

FIG.7A

BUBBLE COUNT METHOD 1 (IN CASE OF NOT USING BUBBLE ID)

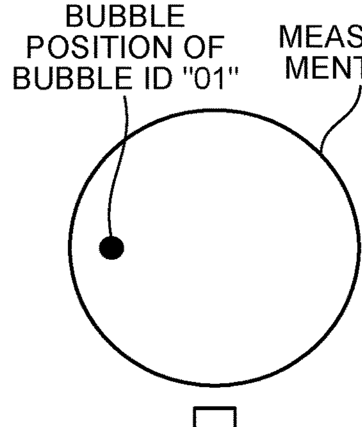

FRAME (t1)
NUMBER OF INFLOW BUBBLES: 1
NUMBER OF OUTFLOW BUBBLES: 0
NUMBER OF INFLOW/ OUTFLOW BUBBLES: 1

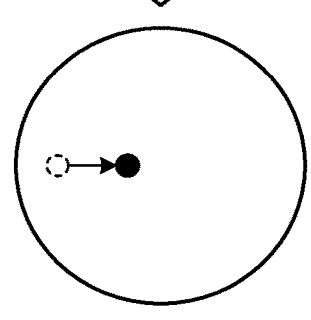

FRAME (t2)
NUMBER OF INFLOW BUBBLES: 1
NUMBER OF OUTFLOW BUBBLES: 0
NUMBER OF INFLOW/ OUTFLOW BUBBLES: 1

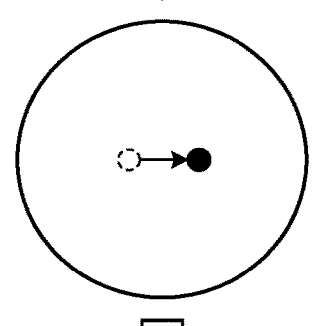

FRAME (t3)
NUMBER OF INFLOW BUBBLES: 0
NUMBER OF OUTFLOW BUBBLES: 1
NUMBER OF INFLOW/ OUTFLOW BUBBLES: 1

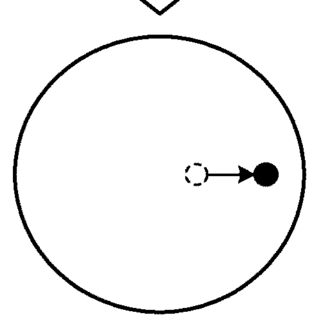

FRAME (t4)
NUMBER OF INFLOW BUBBLES: 0
NUMBER OF OUTFLOW BUBBLES: 1
NUMBER OF INFLOW/ OUTFLOW BUBBLES: 1

FRAME (t1 TO t4)
NUMBER OF INFLOW BUBBLES: 2
NUMBER OF OUTFLOW BUBBLES: 2
NUMBER OF INFLOW/ OUTFLOW BUBBLES: 4

FIG.7B

BUBBLE COUNT METHOD 2 (IN CASE OF USING BUBBLE ID)

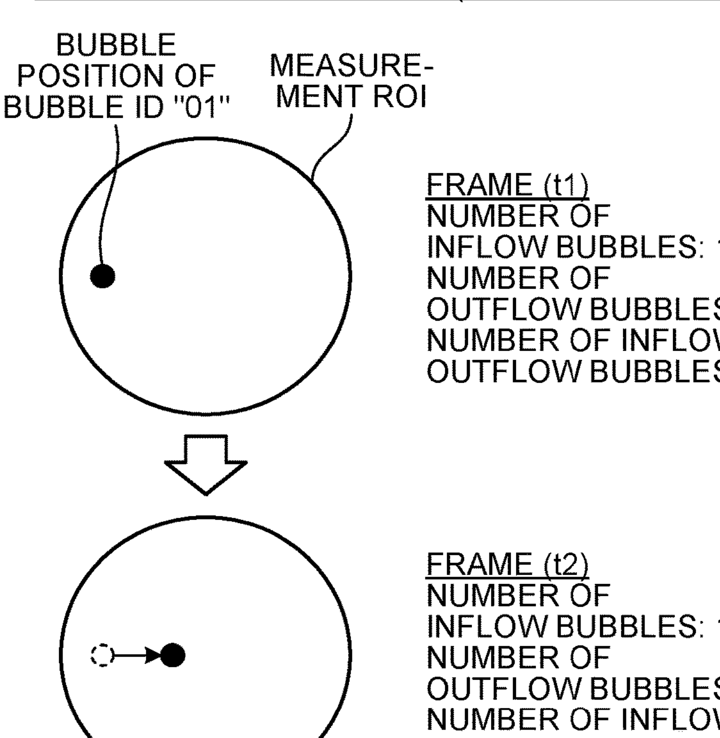

FRAME (t1)
NUMBER OF INFLOW BUBBLES: 1
NUMBER OF OUTFLOW BUBBLES: 0
NUMBER OF INFLOW/OUTFLOW BUBBLES: 1

FRAME (t2)
NUMBER OF INFLOW BUBBLES: 1
NUMBER OF OUTFLOW BUBBLES: 0
NUMBER OF INFLOW/OUTFLOW BUBBLES: 1

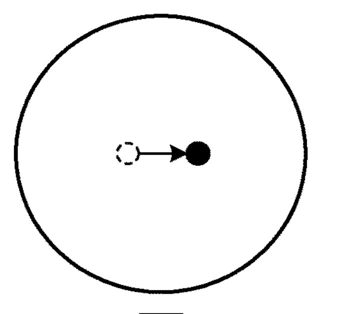

FRAME (t3)
NUMBER OF INFLOW BUBBLES: 0
NUMBER OF OUTFLOW BUBBLES: 1
NUMBER OF INFLOW/OUTFLOW BUBBLES: 1

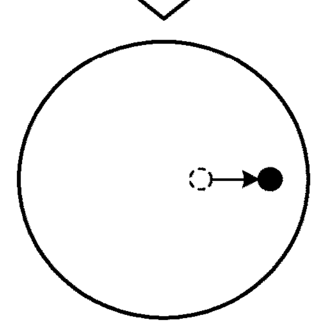

FRAME (t4)
NUMBER OF INFLOW BUBBLES: 0
NUMBER OF OUTFLOW BUBBLES: 1
NUMBER OF INFLOW/OUTFLOW BUBBLES: 1

FRAME (t1 TO t4)
NUMBER OF INFLOW BUBBLES: 1
NUMBER OF OUTFLOW BUBBLES: 1
NUMBER OF INFLOW/OUTFLOW BUBBLES: 2

FRAME (t5 TO t7)
NUMBER OF
INFLOW BUBBLES: 6
NUMBER OF
OUTFLOW BUBBLES: 2
NUMBER OF
INFLOW/OUTFLOW BUBBLES: 8
INFLOW BUBBLE RATIO: 0.75
OUTFLOW BUBBLE RATIO: 0.25

MEDICAL IMAGE PROCESSING DEVICE AND COMPUTER PROGRAM PRODUCT

CROSS-REFERENCE TO RELATED APPLICATIONS

This application is based upon and claims the benefit of priority from Japanese Patent Application No. 2020-185354, filed on Nov. 5, 2020; the entire contents of which are incorporated herein by reference.

FIELD

Embodiments described herein relate generally to a medical image processing device and a computer program product.

BACKGROUND

Conventionally, ultrasonic diagnostic devices perform a contrast echo method that is called Contrast Harmonic Imaging (CHI). In the contrast echo method, for example, imaging is performed by injecting a contrast medium into a vein in an examination of a heart, a liver, and the like. For most of contrast media used in the contrast echo method, minute air bubbles (micro bubbles) are used as reflection sources. With the contrast echo method, for example, a blood vessel in a subject can be clearly delineated.

There is known a technique of displaying a track of a bubble by tracking an individual micro bubble (hereinafter, also simply referred to as a "bubble") included in the contrast medium on a time-series image. In this technique, a moving speed and a moving direction of a bubble can be analyzed by calculating a motion vector of an individual bubble.

BRIEF DESCRIPTION OF THE DRAWINGS

FIG. 7A and FIG. 7B are diagrams for explaining processing performed by the second calculation function according to the embodiment;

DETAILED DESCRIPTION

A medical image processing device according to an embodiment includes processing circuitry. The processing circuitry detects a contrast medium from a medical image. The processing circuitry sets a first region of interest and a second region of interest in the medical image. The processing circuitry calculates a density ratio between a density of a contrast medium included in the first region of interest and a density of a contrast medium included in the second region of interest.

The following describes a medical image processing device and a medical image processing program according to the embodiment with reference to the drawings. The embodiment is not limited to the following embodiment. Basically, content described in one embodiment can also be similarly applied to another embodiment.

In the following embodiment, an ultrasonic diagnostic device is described as an example of the medical image processing device, but the embodiment is not limited thereto. For example, in addition to the ultrasonic diagnostic device, a medical image diagnostic device such as an X-ray diagnostic device, an X-ray Computed Tomography (CT) device, a Magnetic Resonance Imaging (MRI) device, a Single Photon Emission Computed Tomography (SPECT) device, a Positron Emission computed Tomography (PET) device, an SPECT-CT device in which a SPECT device and an X-ray CT device are integrated, a PET-CT device in which a PET device and an X-ray CT device are integrated, or a group of these devices can be applied as the medical image processing device. The medical image processing device is not limited to the medical image diagnostic device, and an optional information processing device can be applied.

Embodiment

Figure 1:
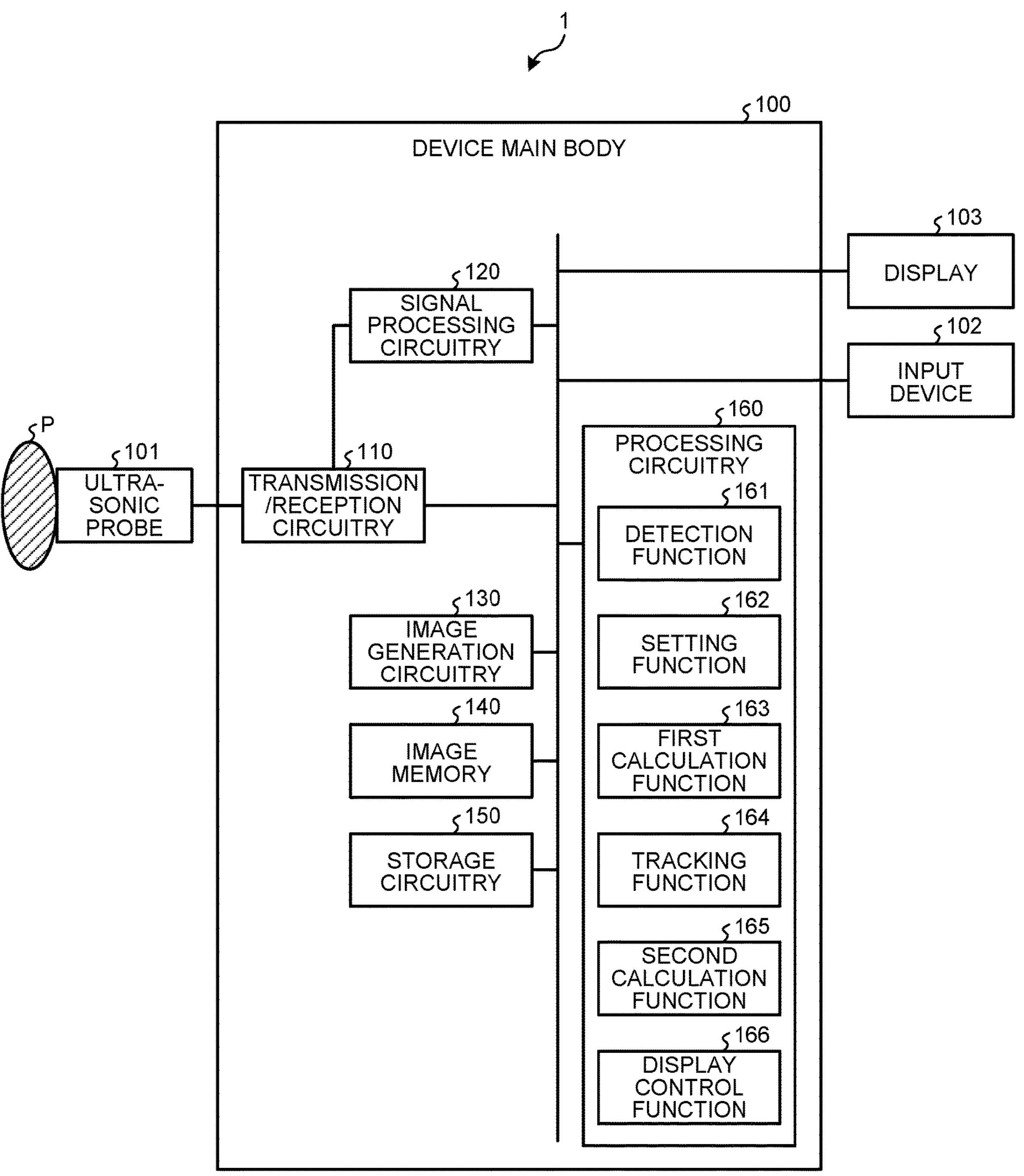
FIG. 1 is a block diagram illustrating a configuration example of an ultrasonic diagnostic device according to an embodiment.

FIG. 1 is a block diagram illustrating a configuration example of an ultrasonic diagnostic device 1 according to the embodiment. As illustrated in FIG. 1, the ultrasonic diagnostic device 1 according to the embodiment includes a device main body 100, an ultrasonic probe 101, an input device 102, and a display 103. The ultrasonic probe 101, the input device 102, and the display 103 are connected to the device main body 100. A subject P is not included in the configuration of the ultrasonic diagnostic device 1.

The ultrasonic probe 101 includes a plurality of transducer elements (for example, piezoelectric transducer elements), and the transducer elements generate ultrasonic waves based on a drive signal supplied from transmission/reception circuitry 110 included in the device main body 100 (described later). The transducer elements included in the ultrasonic probe 101 receive reflected waves from the subject P, and convert the reflected waves into electric signals. The ultrasonic probe 101 also includes a matching layer disposed in the transducer element, a backing material that prevents ultrasonic waves from propagating rearward from the transducer element, and the like.

When the ultrasonic waves are transmitted from the ultrasonic probe 101 to the subject P, the transmitted ultrasonic waves are successively reflected by a discontinuous surface of acoustic impedance in body tissues of the subject P, and received as reflected wave signals (echo signals) by the transducer elements included in the ultrasonic probe 101. Amplitude of the received reflected wave signals depends on a difference in the acoustic impedance on the discontinuous surface by which the ultrasonic waves are reflected. In a case in which a transmitted ultrasonic pulse is reflected by a surface of a moving blood flow, a cardiac wall, and the like, the reflected wave signal depends on a speed component with respect to an ultrasonic wave transmitting direction of a mobile object, and is subjected to frequency shift due to the Doppler effect.

The embodiment can be applied to any of a case in which the ultrasonic probe 101 illustrated in FIG. 1 is a one-dimensional ultrasonic probe in which the piezoelectric transducer elements are disposed in a line, a case in which the ultrasonic probe 101 illustrated in FIG. 1 is a one-dimensional ultrasonic probe in which the piezoelectric transducer elements disposed in a line are mechanically oscillated, and a case in which the ultrasonic probe 101 illustrated in FIG. 1 is a two-dimensional ultrasonic probe in which the piezoelectric transducer elements are two-dimensionally disposed in a grid-like fashion.

The input device 102 includes a mouse, a keyboard, a button, a panel switch, a touch command screen, a foot switch, a trackball, a joy stick, and the like, receives various setting requests from an operator of the ultrasonic diagnostic device 1, and transfers the received various setting requests to the device main body 100.

The display 103 displays a Graphical User Interface (GUI) for inputting various setting requests using the input device 102 by the operator of the ultrasonic diagnostic device 1, or displays ultrasonic image data and the like generated in the device main body 100.

The device main body 100 is a device that generates ultrasonic image data based on a reflected wave signal received by the ultrasonic probe 101, and includes the transmission/reception circuitry 110, signal processing circuitry 120, image generation circuitry 130, an image memory 140, storage circuitry 150, and processing circuitry 160 as illustrated in FIG. 1. The transmission/reception circuitry 110, the signal processing circuitry 120, the image generation circuitry 130, the image memory 140, the storage circuitry 150, and the processing circuitry 160 are connected to each other in a communicable manner.

The transmission/reception circuitry 110 includes a pulse generator, a transmission delay unit, a pulser, and the like, and supplies a drive signal to the ultrasonic probe 101. The pulse generator repeatedly generates rate pulses for forming transmission ultrasonic waves at a predetermined rate frequency. The transmission delay unit focuses ultrasonic waves generated from the ultrasonic probe 101 into a beam shape, and gives a delay time for each piezoelectric transducer element required for determining transmission directivity to each rate pulse generated by the pulse generator. The pulser applies a drive signal (drive pulse) to the ultrasonic probe 101 at a timing based on the rate pulse. That is, by changing the delay time given to each rate pulse, the transmission delay unit optionally adjusts a transmitting direction of ultrasonic waves transmitted from a surface of the piezoelectric transducer element.

The transmission/reception circuitry 110 has a function that can instantaneously change a transmission frequency, a transmission driving voltage, and the like for performing a predetermined scan sequence based on an instruction from the processing circuitry 160 (described later). Specifically, change of the transmission driving voltage is implemented by transmission circuitry of a linear amplifier type that can instantaneously change a value thereof, or a mechanism of electrically switching between a plurality of power supply units.

The transmission/reception circuitry 110 also includes a pre-amplifier, an analog/digital (A/D) converter, a reception delay unit, an adder, and the like, and performs various kinds of processing on the reflected wave signal received by the ultrasonic probe 101 to generate reflected wave data. The pre-amplifier amplifies the reflected wave signal for each channel. The A/D converter A/D-converts the amplified reflected wave signal. The reception delay unit gives a delay time required for determining reception directivity. The adder performs addition processing for the reflected wave signal processed by the reception delay unit, and generates reflected wave data. Through the addition processing performed by the adder, a reflection component from a direction corresponding to the reception directivity of the reflected wave signal is enhanced, and a comprehensive beam of transmission/reception of ultrasonic waves is formed due to the reception directivity and the transmission directivity.

In a case of scanning a two-dimensional region of the subject P, the transmission/reception circuitry 110 causes the ultrasonic probe 101 to transmit an ultrasonic beam in a two-dimensional direction. The transmission/reception circuitry 110 then generates two-dimensional reflected wave data from the reflected wave signal received by the ultrasonic probe 101. In a case of scanning a three-dimensional region of the subject P, the transmission/reception circuitry 110 causes the ultrasonic probe 101 to transmit an ultrasonic beam in a three-dimensional direction. The transmission/reception circuitry 110 then generates three-dimensional reflected wave data from the reflected wave signal received by the ultrasonic probe 101.

For example, the signal processing circuitry 120 performs logarithmic amplification, envelope detection processing, and the like on the reflected wave data received from the transmission/reception circuitry 110, and generates data in which signal strength for each sample point is represented by a degree of luminance (B-mode data). The B-mode data generated by the signal processing circuitry 120 is output to the image generation circuitry 130.

The signal processing circuitry 120 can change a frequency band for visualization by changing a detection frequency through filter processing. By using this function of the signal processing circuitry 120, the contrast echo method, for example, Contrast Harmonic Imaging (CHI) can be performed. That is, the signal processing circuitry 120 can separate reflected wave data (a harmonic component or a subharmonic component) the reflection sources of which are minute air bubbles (micro bubbles) as a contrast medium, and reflected wave data (a fundamental wave component) the reflection sources of which are tissues inside the subject P from the reflected wave data of the subject P into which the contrast medium is injected. Due to this, the signal processing circuitry 120 can extract the harmonic component or the subharmonic component from the reflected wave data of the subject P, and generate the B-mode data for generating contrast image data. The B-mode data for generating the contrast image data is data representing, by luminance, signal strength of a reflected wave the reflection source of which is the contrast medium. The signal processing circuitry 120 can also generate the B-mode data for generating tissue image data by extracting a fundamental wave component from the reflected wave data of the subject P.

When performing CHI, the signal processing circuitry 120 can extract a harmonic component using a method different from the method of using the filter processing described above. In harmonic imaging, an imaging method that is called an Amplitude Modulation (AM) method, a Phase Modulation (PM) method, or an AMPM method that is a combination of the AM method and the PM method is performed. In the AM method, the PM method, and the AMPM method, ultrasonic wave transmission is performed multiple times (at multiple rates) using different amplitudes or different phases with respect to the same scanning line. Due to this, the transmission/reception circuitry 110 generates and outputs a plurality of pieces of the reflected wave data for each scanning line. The signal processing circuitry 120 then performs addition and subtraction processing corresponding to a modulation method on the pieces of reflected wave data for respective scanning lines to extract the harmonic component. The signal processing circuitry 120 then performs envelope detection processing and the like on the reflected wave data of the harmonic component, and generates the B-mode data.

For example, in a case in which the PM method is performed, the transmission/reception circuitry 110 causes ultrasonic waves of the same amplitude in which phase polarity is reversed like (−1, 1), for example, to be transmitted two times for each scanning line through a scan sequence set by the processing circuitry 160. The transmission/reception circuitry 110 then generates reflected wave data obtained by transmitting "−1" and reflected wave data obtained by transmitting "1", and the signal processing circuitry 120 adds up these two pieces of the reflected wave data. Due to this, generated is a signal in which the fundamental wave component is removed, and a second-order harmonic component mainly remains. The signal processing circuitry 120 then performs envelope detection processing and the like on this signal, and generates B-mode data for CHI (B-mode data for generating contrast image data). The B-mode data for CHI is data representing, by luminance, signal strength of a reflected wave the reflection source of which is the contrast medium. In a case in which the PM method is performed in CHI, the signal processing circuitry 120 can generate the B-mode data for generating tissue image data by performing filter processing on the reflected wave data obtained by transmitting "1", for example.

For example, the signal processing circuitry 120 generates data (Doppler data) obtained by extracting motion information based on the Doppler effect of a mobile object from the reflected wave data received from the transmission/reception circuitry 110 for each sample point in a scanning region. Specifically, the signal processing circuitry 120 performs frequency analysis on speed information based on the reflected wave data, extracts a blood flow, a tissue, and a contrast medium echo component due to the Doppler effect, and generates data (Doppler data) obtained by extracting mobile object information such as an average speed, dispersion, and power for multiple points. Herein, the mobile object is a blood flow, a tissue such as a cardiac wall, or a contrast medium, for example. The motion information (blood flow information) obtained by the signal processing circuitry 120 is transmitted to the image generation circuitry 130, and displayed in color on the display 103 as an average speed image, a dispersion image, a power image, or a combination image thereof.

The image generation circuitry 130 generates ultrasonic image data from the data generated by the signal processing circuitry 120. The image generation circuitry 130 generates B-mode image data from the B-mode data generated by the signal processing circuitry 120, the B-mode image data representing strength of the reflected wave by luminance. The image generation circuitry 130 also generates Doppler image data representing the mobile object information from the Doppler data generated by the signal processing circuitry 120. The Doppler image data is speed image data, dispersion image data, power image data, or image data obtained by combining them.

Typically, the image generation circuitry 130 converts (scan converts) a scanning line signal string of ultrasonic scanning into a scanning line signal string of a video format represented by a television and the like, and generates ultrasonic image data for display. Specifically, the image generation circuitry 130 performs coordinate transformation in accordance with a scanning mode for ultrasonic waves by the ultrasonic probe 101 to generate ultrasonic image data for display. As various kinds of image processing other than the scan conversion, for example, the image generation circuitry 130 performs image processing (smoothing processing) for regenerating an average value image of luminance by using a plurality of image frames after the scan conversion, image processing (edge emphasis processing) by using a differential filter in an image, and the like. The image generation circuitry 130 also synthesizes the ultrasonic image data with accessory information (character information of various parameters, divisions, a body mark, and the like).

That is, the B-mode data and the Doppler data are ultrasonic image data before the scan conversion processing, and the data generated by the image generation circuitry 130 is ultrasonic image data for display after the scan conversion processing. In a case in which the signal processing circuitry 120 generates three-dimensional data (three-dimensional B-mode data and three-dimensional Doppler data), the image generation circuitry 130 performs coordinate transformation in accordance with the scanning mode for ultrasonic waves by the ultrasonic probe 101 to generate volume data. The image generation circuitry 130 then performs various kinds of rendering processing on the volume data, and generates two-dimensional image data for display.

The image memory 140 is a memory that stores the image data for display generated by the image generation circuitry 130. The image memory 140 can also store data generated by the signal processing circuitry 120. The B-mode data or the Doppler data stored in the image memory 140 can be called by the operator after a diagnosis, for example, and becomes ultrasonic image data for display via the image generation circuitry 130.

The storage circuitry 150 stores various kinds of data such as a control program for performing transmission/reception of ultrasonic waves, image processing, and display processing, diagnostic information (for example, a patient ID, and findings of a doctor), a diagnostic protocol, and various body marks. The storage circuitry 150 is also used for keeping image data stored in the image memory 140 as needed. The data stored in the storage circuitry 150 can be transferred to an external device via an interface (not illustrated).

The processing circuitry 160 controls the entire processing performed by the ultrasonic diagnostic device 1. Specifically, the processing circuitry 160 controls processing performed by the transmission/reception circuitry 110, the signal processing circuitry 120, and the image generation circuitry 130 based on various setting requests input by the operator via the input device 102, and various control programs and various kinds of data read from the storage circuitry 150. The processing circuitry 160 also performs control so that the ultrasonic image data for display stored in the image memory 140 is displayed by the display 103.

As illustrated in FIG. 1, the processing circuitry 160 executes a detection function 161, a setting function 162, a first calculation function 163, a tracking function 164, a second calculation function 165, and a display control function 166. For example, respective processing functions executed by the detection function 161, the setting function 162, the first calculation function 163, the tracking function 164, the second calculation function 165, and the display control function 166 as constituent elements of the processing circuitry 160 illustrated in FIG. 1 are recorded in a storage device (for example, the storage circuitry 150) of the ultrasonic diagnostic device 1 as computer-executable programs. The processing circuitry 160 is a processor that implements a function corresponding to each computer program by reading out each computer program from the storage device to be executed. In other words, the processing circuitry 160 that has read out each computer program is assumed to have each function illustrated in the processing circuitry 160 in FIG. 1. The respective processing functions executed by the detection function 161, the setting function 162, the first calculation function 163, the tracking function 164, the second calculation function 165, and the display control function 166 will be described later.

In FIG. 1, the single processing circuitry 160 is assumed to implement the processing functions executed by the detection function 161, the setting function 162, the first calculation function 163, the tracking function 164, the second calculation function 165, and the display control function 166. Alternatively, the processing circuitry may be configured by combining a plurality of independent processors, and each of the processors may implement a function by executing a computer program.

A basic configuration of the ultrasonic diagnostic device 1 according to the embodiment has been described above. With this configuration, the ultrasonic diagnostic device 1 according to the embodiment can provide an index value based on distribution of the contrast medium through processing described below.

For example, the ultrasonic diagnostic device 1 detects and tracks each of minute air bubbles (micro bubbles) used as the contrast medium in the contrast echo method. The ultrasonic diagnostic device 1 then calculates an index value based on distribution of the contrast medium based on a detection result and/or a tracking result. Hereinafter, the contrast medium is also referred to as a “contrast medium bubble” or a “bubble”.

In the following embodiment, described is a case in which tracking processing for a bubble is performed, but the embodiment is not limited thereto. For example, even in a case in which the tracking processing for a bubble is not performed, the index value based on distribution of the contrast medium can be calculated.

In the following embodiment, described is a case of delineating a flow of the contrast medium by performing processing in substantially real time on a medical image (ultrasonic image) that is taken by injecting the contrast medium into the subject P. However, the embodiment is not limited thereto. For example, the processing can be performed later on an ultrasonic image (or reflected wave data and the like) that has been photographed.

Figure 2:
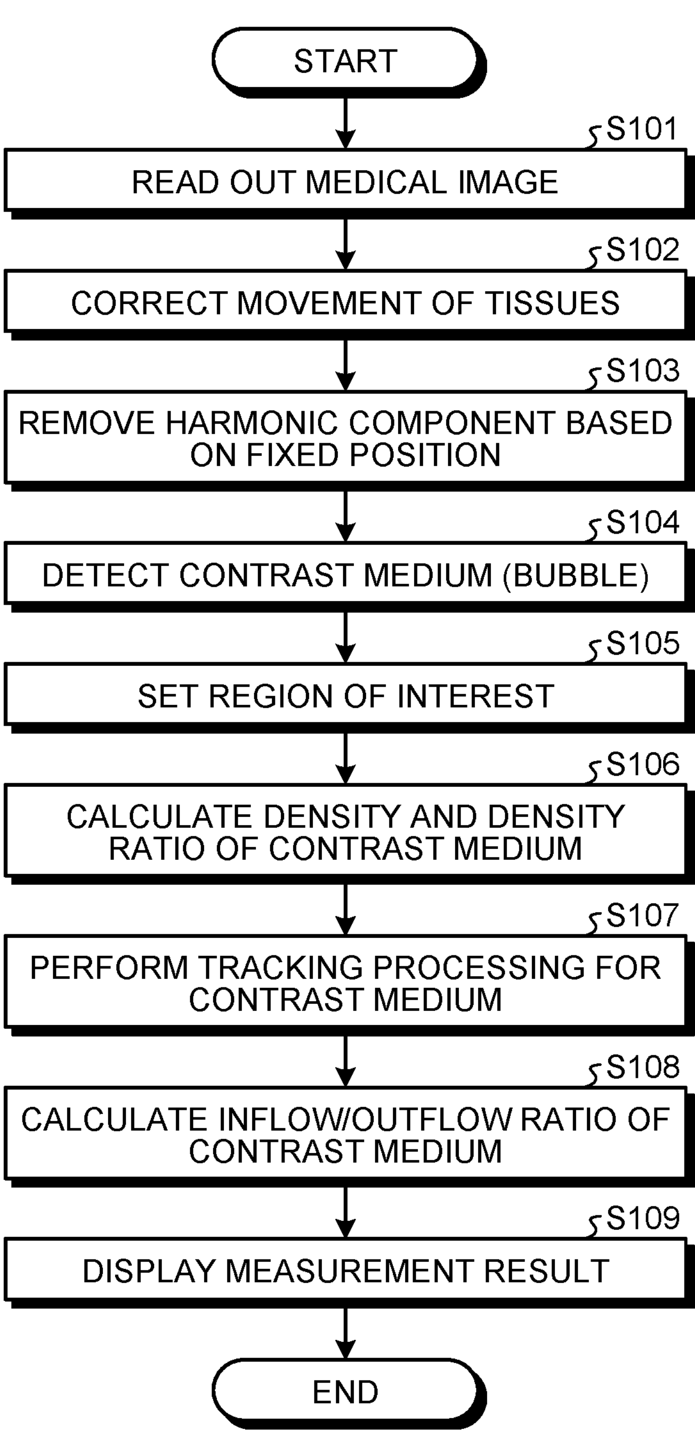
FIG. 2 is a flow chart for explaining a processing procedure performed by the ultrasonic diagnostic device according to the embodiment.

With reference to FIG. 2, the following describes a processing procedure performed by the ultrasonic diagnostic device 1 according to the embodiment. FIG. 2 is a flow chart for explaining the processing procedure performed by the ultrasonic diagnostic device 1 according to the embodiment. Description about FIG. 2 will be made with reference to FIG. 3 to FIG. 9B.

The processing procedure illustrated in FIG. 2 is started in a case of receiving a request for calculating the index value from the operator, for example. The processing procedure illustrated in FIG. 2 will not be started until the request for calculation is received, and is in a standby state.

As illustrated in FIG. 2, the detection function 161 reads out a medical image (step S101). For example, the detection function 161 reads out, as medical images, a plurality of ultrasonic images arranged in time series from the image memory 140. The ultrasonic image is, for example, a contrast image that is taken by injecting the contrast medium into the subject P.

In a normal contrast echo method, a contrast medium of an amount with which micro bubbles overlap with each other is injected to clearly delineate a blood vessel of the subject P. On the other hand, in the present embodiment, if the micro bubbles overlap with each other, individual bubbles cannot be detected. Thus, in the present embodiment, a smaller amount of contrast medium is injected as compared with a case of the normal contrast echo method. The amount of the contrast medium is preferably determined depending on a thickness of a blood vessel or a blood flow rate in a strict sense, but may be determined depending on a part to be imaged. The amount of the contrast medium may be gradually increased at the time of being actually injected.

Subsequently, the detection function 161 corrects movement of tissues (step S102). For example, the detection function 161 calculates a correction amount for matching a coordinate system of an ultrasonic image of the N-th frame with a coordinate system of an ultrasonic image of the (N−1)-th frame. The detection function 161 then corrects the coordinate system of the ultrasonic image of the N-th frame using the calculated correction amount. The detection function 161 corrects movement of tissues for each of the ultrasonic images arranged in time series.

The detection function 161 then removes a harmonic component based on a fixed position (step S103). For example, the detection function 161 removes a harmonic component based on a fixed position on the basis of statistical processing for a signal in a frame direction for the ultrasonic image after correcting movement of tissues. The detection function 161 removes the harmonic component based on the fixed position for each of the ultrasonic images arranged in time series.

The detection function 161 then detects the contrast medium (bubble) (step S104). For example, the detection function 161 detects the contrast medium from the medical image. As a specific example, the detection function 161 detects, as a bubble position, a region having a luminance value equal to or larger than a predetermined threshold in the ultrasonic image from which the harmonic component is removed. The detection function 161 detects the bubble for each of the ultrasonic images arranged in time series. A method of detecting the bubble is not limited thereto. For example, the bubble can be detected through well-known detection processing such as image analysis processing using a shape of the bubble.

The setting function 162 sets a region of interest (ROI) (step S105). For example, the setting function 162 sets a first region of interest and a second region of interest in the medical image. Herein, the first region of interest and the second region of interest are regions at least partially overlapping with each other. More preferably, the first region of interest is a region encompasses the second region of interest. Processing performed by the setting function 162 will be described later with reference to FIG. 3.

The first calculation function 163 calculates a density and a density ratio of the contrast medium (step S106). For example, the first calculation function 163 counts the number of bubbles in the first region of interest, and the number of bubbles in the second region of interest. The first calculation function 163 then calculates a bubble density in the first region of interest based on the number of bubbles in the first region of interest and an area of the first region of interest. The first calculation function 163 also calculates a bubble density in the second based on the number of bubbles in the second region of interest and an area of the second region of interest. The first calculation function 163 then calculates a density ratio between the density of the contrast medium included in the first region of interest and the density of the contrast medium included in the second region of interest.

Figure 3:
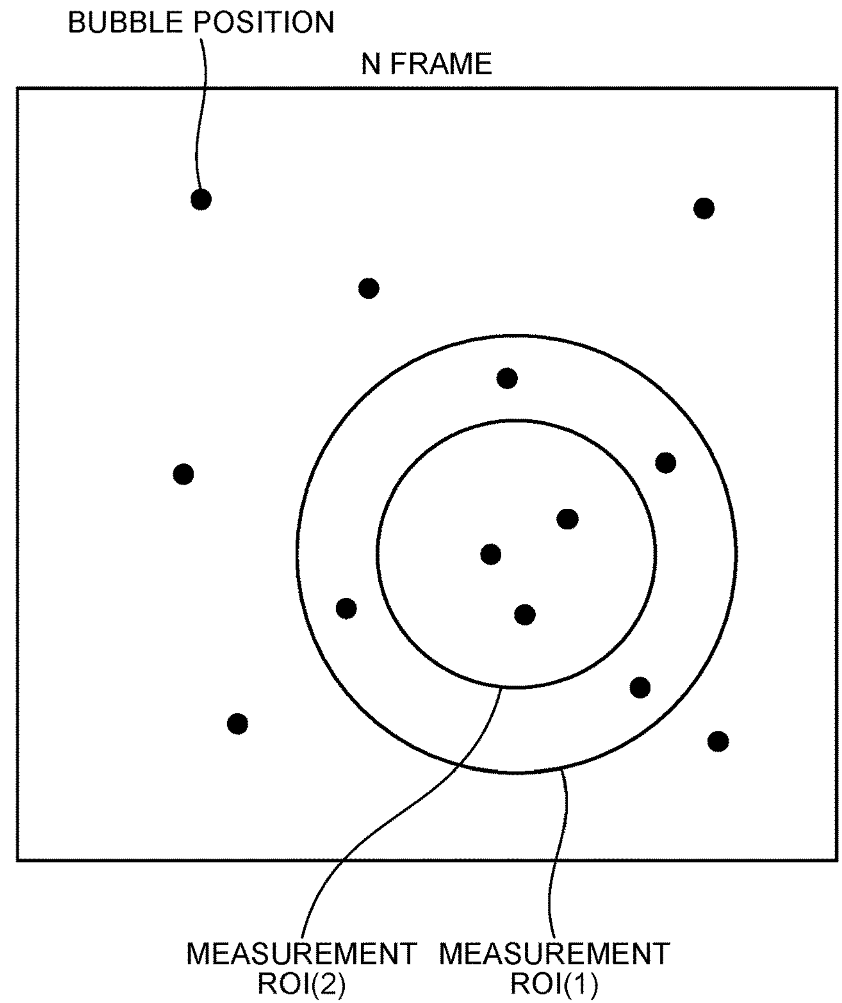
FIG. 3 is a diagram for explaining processing performed by a setting function and a first calculation function according to the embodiment.

With reference to FIG. 3, the following describes processing performed by the setting function 162 and the first calculation function 163 according to the embodiment. FIG. 3 is a diagram for explaining the processing performed by the setting function 162 and the first calculation function 163 according to the embodiment. FIG. 3 exemplifies a contrast image of the N-th frame. In FIG. 3, a black dot mark indicates a position of an individual bubble.

As illustrated in FIG. 3, the setting function 162 sets a measurement ROI(1) and a measurement ROI(2). The measurement ROI(1) is preferably set along an outline of a structure delineated in the medical image such as a tumor, for example. For example, the setting function 162 sets the measurement ROI(1) through segmentation processing for the ultrasonic image.

The setting function 162 also sets, as the measurement ROI(2), a region obtained by reducing the measurement ROI(1) by a predetermined size. For example, the setting function 162 calculates a center (centroid) of the measurement ROI(1). The setting function 162 then sets the measurement ROI(2) by causing a distance from the centroid to each point on the measurement ROI(1) to be 50%.

The first calculation function 163 then sets an inner circle region and an outer circle region as measurement ROIs as calculation targets of the index value. The inner circle region is a region inside the measurement ROI(2). The outer circle region is a region having an annular shape excluding the measurement ROI(2) from the measurement ROI(1). In other words, the outer circle region is a region having an annular shape surrounding the inner circle region. The outer circle region is an example of the first region of interest. The inner circle region is an example of the second region of interest.

The first calculation function 163 then calculates a bubble density [/cm^2] of each of the inner circle region and the outer circle region using the following expression (1). In the expression (1), "total number of bubbles in the measurement ROI" is a count value of bubbles detected inside a target region. An "area of the measurement ROI" is an area of the inside of the target region.

$$\text{BUBBLE DENSITY } [/\text{cm}^2] = \frac{\text{TOTAL NUMBER OF BUBBLES IN MEASUREMENT } ROI}{\text{AREA OF MEASUREMENT } ROI} \quad (1)$$

For example, in FIG. 3, the number of bubbles in the inner circle region is "3". The first calculation function 163 calculates the bubble density in the inner circle region by dividing "3" by an area of the inner circle region. In FIG. 3, the number of bubbles in the outer circle region is "4". The first calculation function 163 calculates the bubble density in the outer circle region by dividing "4" by an area of the outer circle region.

The first calculation function 163 then calculates a bubble density rate by taking a ratio between the bubble density in the inner circle region and the bubble density in the outer circle region. For example, the first calculation function 163 calculates a bubble density ratio by dividing the bubble density in the outer circle region by the bubble density in the inner circle region.

In this way, for each of the ultrasonic images arranged in time series, the first calculation function 163 calculates the bubble density in each measurement ROI and the bubble density ratio.

The content described in FIG. 3 is merely an example, and the embodiment is not limited thereto. For example, in FIG. 3, exemplified is a case in which the measurement ROI(1) and the measurement ROI(2) are automatically set. Alternatively, the measurement ROI(1) and the measurement ROI(2) may be manually set by the operator.

In FIG. 3, exemplified is a case in which the measurement ROI(1) is set along the outline of the tumor, but the embodiment is not limited thereto. For example, the measurement ROI(1) may be set along an outline of an optional structure delineated in the medical image, or may be optionally set by the operator irrespective of the structure.

In FIG. 3, exemplified is a case of calculating the centroid of the measurement ROI(1) as the center, but the embodiment is not limited thereto. For example, an intersection point of a longitudinal direction and a lateral direction of the measurement ROI(1) may be assumed to be the center. The center of the measurement ROI(1) is not necessarily automatically set, but may be manually set by the operator.

In FIG. 3 exemplified is a case in which the measurement ROI(2) is set by causing the distance from the centroid to each point on the measurement ROI(1) to be 50%, but this ratio can be optionally changed. Alternatively, the measurement ROI(2) may be set by reducing the distance by a predetermined distance instead of setting the distance with a percentage.

In FIG. 3, the outer circle region is set as a region having an annular shape excluding the measurement ROI(2) from the measurement ROI(1), but the embodiment is not limited thereto. For example, the first calculation function 163 may set a region (including the measurement ROI(2)) inside the measurement ROI(l) as the outer circle region (first region of interest).

In FIG. 3, as the bubble density ratio, used is the value obtained by dividing the bubble density in the outer circle region by the bubble density in the inner circle region, but the embodiment is not limited thereto. For example, the bubble density ratio may be a value obtained by dividing the bubble density in the inner circle region by the bubble density in the outer circle region.

Returning to the description about FIG. 2, the tracking function 164 performs tracking processing for the contrast medium (step S107). For example, the tracking function 164 calculates a motion vector representing movement of the contrast medium by tracking a position of the contrast medium in each of the medical images arranged in time series.

Figure 4:
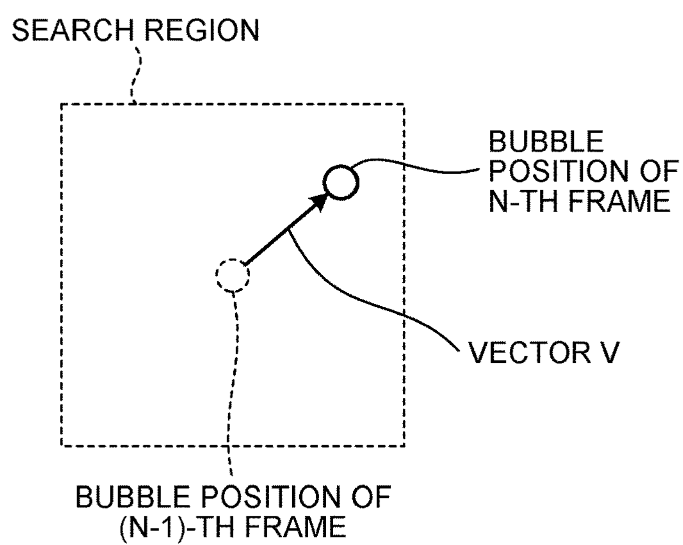
FIG. 4 is a diagram for explaining processing performed by a tracking function according to the embodiment.

With reference to FIG. 4, the following describes processing performed by the tracking function 164 according to the embodiment. FIG. 4 is a diagram for explaining the processing performed by the tracking function 164 according to the embodiment. With reference to FIG. 4, described is a case of tracking movement of a certain bubble from the (N−1)-th frame to the N-th frame.

As illustrated in FIG. 4, the tracking function 164 sets a search region (a dashed line region in FIG. 4) in the ultrasonic image of the N-th frame based on a bubble position in the (N−1)-th frame. This search region is, for example, a rectangular region centered on the bubble position in the (N−1)-th frame, and a size thereof is set based on a distance by which the bubble can move during one frame.

The tracking function 164 then identifies the bubble position present in the search region as a bubble position after the bubble of the (N−1)-th frame moves, and assigns the same (common) identification information (bubble ID) to both bubble positions. The tracking function 164 then calculates a vector V representing movement from the bubble position in the (N−1)-th frame to the bubble position in the N-th frame as a motion vector of this bubble.

In this way, the tracking function 164 performs tracking processing on all bubbles detected from the respective ultrasonic images arranged in time series. Due to this, the tracking function 164 can track generation, movement, and disappearance of the respective bubbles.

The content described in FIG. 4 is merely an example, and the embodiment is not limited thereto. For example, the technique described in JP 2018-015155 A can be optionally applied as the tracking processing. In FIG. 4, exemplified is a case in which the number of bubbles detected from the search region of the N-th frame is "one", but the number is not limited to "one". For example, the number of bubbles in the search region is "two or more", it is preferable to specify one bubble based on moving distances or similarity in shapes of the bubbles. In a case in which no bubble is present in the search region, it is preferable to identify that the bubbles have disappeared.

Returning to the description about FIG. 2, the second calculation function 165 calculates an inflow/outflow ratio of the contrast medium (step S108). For example, the second calculation function 165 identifies whether each bubble in the region of interest is an inflow bubble or an outflow bubble based on the motion vector of each bubble. The second calculation function 165 then calculates the inflow/outflow ratio of the bubbles in the region of interest based on the number of inflow bubbles and the number of outflow bubbles.

A calculation target region (measurement ROI) of the inflow/outflow ratio is preferably set along an outline of an optional structure such as a tumor. Thus, typically, the measurement ROI(1) set at step S105 is preferably applied as the calculation target region of the inflow/outflow ratio, but the embodiment is not limited thereto. For example, the calculation target region of the inflow/outflow ratio may be set separately from the calculation target region of the bubble density.

The following describes processing performed by the second calculation function 165 according to the embodiment with reference to FIG. 5 to FIG. 8. FIG. 5 to FIG. 8 are diagrams for explaining the processing performed by the second calculation function 165 according to the embodiment.

Figure 5:
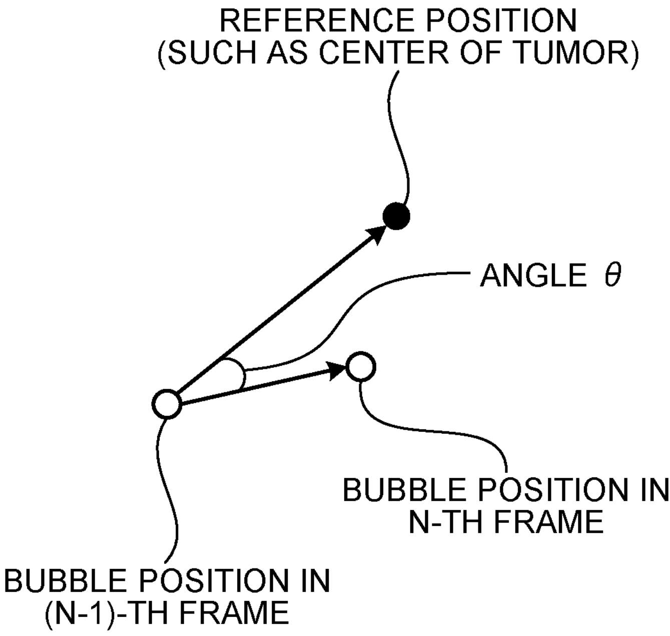
FIG. 5 is a diagram for explaining processing performed by a second calculation function according to the embodiment.

First, as illustrated in FIG. 5, the second calculation function 165 calculates an angle θ representing a moving direction of the bubble with respect to a reference position for each of the bubbles in the measurement ROI. Herein, the reference position (a black dot mark in FIG. 5) corresponds to the center of the measurement ROI such as a center of a tumor, for example. A method of setting the center of the measurement ROI is the same as that in the description about FIG. 3. The angle θ is represented by an angle formed by a straight line connecting the bubble position in the (N−1)-th frame with the reference position and the motion vector of the bubble of the N-th frame. A value of the angle θ comes closer to 0° as the bubble comes closer to the reference position, and comes closer to 180° (−180°) as the bubble moves away from the reference position.

Figure 6:
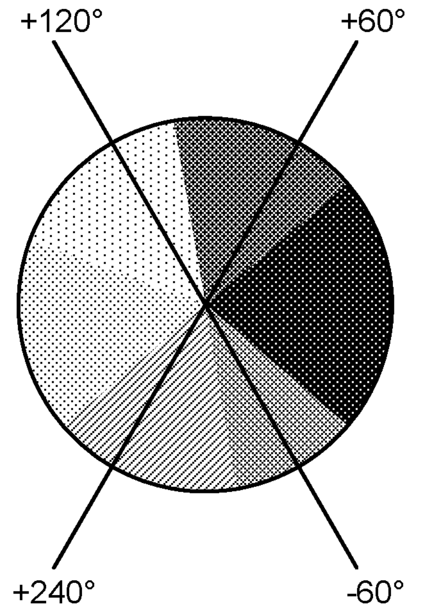
FIG. 6 is a diagram for explaining processing performed by the second calculation function according to the embodiment.

Next, as illustrated in FIG. 6, the second calculation function 165 identifies whether each bubble is an inflow bubble or an outflow bubble based on a moving direction of each bubble. For example, the second calculation function 165 identifies, as the "inflow bubble", a bubble having the angle θ illustrated in FIG. 5 falling within a range from −60° to 60° (from 0° to 60°, from 300° to 360°). The second calculation function 165 also identifies, as the "outflow bubble", a bubble having the angle θ illustrated in FIG. 5 falling within a range from 120° to 240° (from 120° to 180°, from −180° to)−120°. The second calculation function 165 does not identify, as the inflow bubble or the outflow bubble, a bubble not included in any of the angle ranges.

As illustrated in FIG. 7A and FIG. 7B, the second calculation function 165 counts the number of inflow bubbles, the number of outflow bubbles, and the number of inflow/outflow bubbles based on a bubble count method 1 or a bubble count method 2. With reference to FIG. 7A and FIG. 7B, described is a case in which a bubble of the bubble ID "01" moves from a left side toward a right side of the drawing with respect to a certain measurement ROI. In FIG. 7A and FIG. 7B, a frame (t1), a frame (t2), a frame (t3), and a frame (t4) correspond to four continuous frames, respectively. Representation of frames (t1 to t4) represents a section including the frame (t1), the frame (t2), the frame (t3), and the frame (t4).

With reference to FIG. 7A, the following describes the bubble count method 1. The bubble count method 1 is a count method without using the bubble ID. For example, in the frame (t1), the bubble of the bubble ID "01" moves toward the center of the measurement ROI, so that the bubble of the bubble ID "01" is identified to be the "inflow bubble". Thus, in the frame (t1), the number of inflow bubbles is "1", the number of outflow bubbles is "0", and the number of inflow/outflow bubbles is "1". The number of inflow/outflow bubbles (total number) is a sum of the number of inflow bubbles and the number of outflow bubbles.

In the frame (t2), the bubble of the bubble ID "01" moves toward the center of the measurement ROI, so that the bubble of the bubble ID "01" is identified to be the "inflow bubble". Thus, in the frame (t2), the number of inflow bubbles is "1", the number of outflow bubbles is "0", and the number of inflow/outflow bubbles is "1".

In the frame (t3), the bubble of the bubble ID "01" moves away from the center of the measurement ROI, so that the bubble of the bubble ID "01" is identified to be the "outflow bubble". Thus, in the frame (t3), the number of inflow bubbles is "0", the number of outflow bubbles is "1", and the number of inflow/outflow bubbles is "1".

In the frame (t4), the bubble of the bubble ID "01" moves away from the center of the measurement ROI, so that the bubble of the bubble ID "01" is identified to be the "outflow bubble". Thus, in the frame (t4), the number of inflow bubbles is "0", the number of outflow bubbles is "1", and the number of inflow/outflow bubbles is "1".

Cumulative values of the number of inflow bubbles, the number of outflow bubbles, and the number of inflow/outflow bubbles in the frames (t1 to t4) are calculated by adding up values of the respective frames. That is, the cumulative value of the number of inflow bubbles in the frames (t1 to t4) is "2", the cumulative value of the number of outflow bubbles is "2", and the cumulative value of the inflow/outflow bubbles is "4".

Each of average values of the number of inflow bubbles, the number of outflow bubbles, and the number of inflow/outflow bubbles in the frames (t1 to t4) is calculated by dividing a total value (cumulative value) of values of the respective frames by the number of frames. That is, the average value of the number of inflow bubbles in the frames (t1 to t4) is "0.5", the average value of the number of outflow bubbles is "0.5", and the average value of the inflow/outflow bubbles is "1".

With reference to FIG. 7B, the following describes the bubble count method 2. The bubble count method 2 is a count method using the bubble ID. That is, the second calculation function 165 performs calculation while eliminating double-counting of an identical bubble by using the bubble ID. In the bubble count method 2, the values of the number of inflow bubbles, the number of outflow bubbles, and the number of inflow/outflow bubbles in the respective frames are the same as those in the bubble count method 1, so that description thereof will be omitted.

The cumulative value of the number of inflow bubbles in the frames (t1 to t4) is calculated by adding up the number of bubbles identified with the identification information among the inflow bubbles in the frames (t1 to t4). In the example of FIG. 7B, the inflow bubble in the frames (t1 to t4) is only the bubble of the bubble ID "01". That is, the cumulative value of the number of inflow bubbles in the frames (t1 to t4) is "1".

The cumulative value of the number of outflow bubbles in the frames (t1 to t4) is calculated by adding up the number of bubbles identified with the identification information among the outflow bubbles in the frames (t1 to t4). In the example of FIG. 7B, the outflow bubble in the frames (t1 to t4) is only the bubble of the bubble ID "01". That is, the cumulative value of the number of outflow bubbles in the frames (t1 to t4) is "1".

The cumulative value of the number of inflow/outflow bubbles in the frames (t1 to t4) is calculated by adding up the number of inflow bubbles and the number of outflow bubbles in the same section. That is, the cumulative value of the number of inflow/outflow bubbles in the frames (t1 to t4) is "2".

Each of average values of the number of inflow bubbles, the number of outflow bubbles, and the number of inflow/outflow bubbles in the frames (t1 to t4) is calculated by dividing a total value (cumulative value) of values of the respective frames by the number of frames. That is, the average value of the number of inflow bubbles in the frames (t1 to t4) is "0.25", the average value of the number of outflow bubbles is "0.25", and the average value of the inflow/outflow bubbles is "0.5".

In this way, the second calculation function 165 counts the number of inflow bubbles, the number of outflow bubbles, and the number of inflow/outflow bubbles using the bubble count method 1 or the bubble count method 2. The second calculation function 165 then calculates the inflow/outflow ratio for the measurement ROI. Herein, the inflow/outflow ratio is a term that encompasses an inflow ratio (inflow bubble ratio) and an outflow ratio (outflow bubble ratio).

For example, the first calculation function 163 calculates the inflow bubble ratio for a certain measurement ROI using the following expression (2).

$$\text{INFLOW BUBBLE RATIO} = \frac{\text{NUMBER OF INFLOW BUBBLES}}{\text{TOTAL NUMBER OF INFLOW/OUTFLOW BUBBLES}} \quad (2)$$

Figure 8:
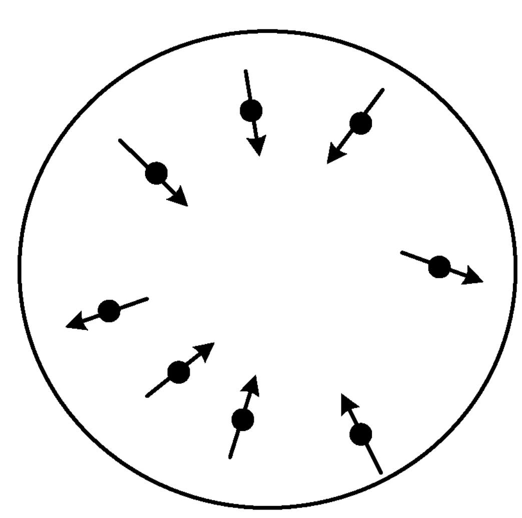
FIG. 8 is a diagram for explaining processing performed by the second calculation function according to the embodiment.

With reference to FIG. 8, the following describes calculation of the inflow/outflow ratio. FIG. 8 exemplifies bubbles detected in an optional measurement ROI (a circle in FIG. 8) and motion vectors of the respective bubbles in a frame (t5), a frame (t6), and a frame (t7). In FIG. 8, the frame (t5), the frame (t6), and the frame (t7) correspond to three continuous frames. Representation of frames (t5 to t7) represents a section including the frame (t5), the frame (t6), and the frame (t7). The frames (t5 to t7) in FIG. 8 are different from the frames (t1 to t4) in FIG. 7A and FIG. 7B.

In the example illustrated in FIG. 8, the number of inflow bubbles is "6", the number of outflow bubbles is "2", and the number of inflow/outflow bubbles is "8". In this case, the second calculation function 165 calculates the inflow bubble ratio of "0.75" by dividing "6" by "8" based on the expression (2).

The second calculation function 165 can also calculate the outflow bubble ratio similarly to the inflow bubble ratio. For example, the second calculation function 165 calculates the outflow bubble ratio "0.25" by dividing the number of outflow bubbles "2" by the number of inflow/outflow bubbles "8".

In this way, the second calculation function 165 calculates the inflow/outflow ratio of the bubbles. The content described in FIG. 5 to FIG. 8 is merely an example, and the embodiment is not limited thereto. For example, the angle ranges for identifying the inflow bubble and the outflow bubble described in FIG. 6 are merely examples, and can be changed to an optional angle range.

In FIG. 7B, exemplified is a case of calculating the cumulative value of the number of inflow/outflow bubbles by adding up the number of inflow bubbles and the number of outflow bubbles, but the embodiment is not limited thereto. For example, the number of inflow/outflow bubbles may be calculated by adding up the number of bubbles identified with the identification information among the inflow bubbles and the outflow bubbles in the frames (t1 to t4). In the example of FIG. 7B, the inflow bubble and the outflow bubble in the frames (t1 to t4) are only the bubble of the bubble ID "01". That is, the cumulative value of the number of inflow/outflow bubbles in the frames (t1 to t4) may be calculated to be "1".

In FIG. 8, exemplified is a case of calculating the inflow/outflow ratio for a section corresponding to three frames, that is, the frames (t5 to t7), but the embodiment is not limited thereto. For example, the second calculation function 165 may calculate the inflow/outflow ratio for a section from a start frame to a current (or the last) frame among the ultrasonic images arranged in time series, or may calculate the inflow/outflow ratio for an optional section. The second calculation function 165 may also calculate the inflow/outflow ratio for an optional one frame, not limited to the section. That is, the second calculation function 165 may calculate, as the inflow/outflow ratio, a value in a predetermined time phase, or a cumulative value or an average value in a predetermined section.

In FIG. 8, exemplified is a case of calculating the cumulative value or the average value without using the bubble ID, but the embodiment is not limited thereto. For example, the second calculation function 165 may calculate the cumulative value or the average value in the predetermined section while eliminating double-counting of an identical bubble. The processing of eliminating double-counting of an identical bubble is the same as that in the description about FIG. 7B.

In FIG. 8, exemplified is a case of calculating the inflow/outflow ratio for an optional measurement ROI, but the embodiment is not limited thereto. For example, the second calculation function 165 may calculate the inflow/outflow ratio for the outer circle region and/or the inner circle region described above. That is, the second calculation function 165 may calculate the inflow/outflow ratio of the contrast medium in at least one of the first region of interest and the second region of interest based on the motion vector.

In the example described above, a denominator of each of the inflow bubble ratio and the outflow bubble ratio is assumed to be the "number of inflow/outflow bubbles", but the embodiment is not limited thereto. For example, the inflow bubble ratio may be a value obtained by dividing the number of inflow bubbles by the number of outflow bubbles. The outflow bubble ratio may be a value obtained by dividing the number of outflow bubbles by the number of inflow bubbles.

Returning to the description about FIG. 2, the display control function 166 displays a measurement result (step S109). For example, the display control function 166 displays information indicating temporal changes in values calculated by the first calculation function 163 and the second calculation function 165. Specifically, the display control function 166 displays information indicating temporal changes in the density or the density ratio. The display control function 166 also displays information indicating temporal changes in the inflow/outflow ratio.

Figure 9A:
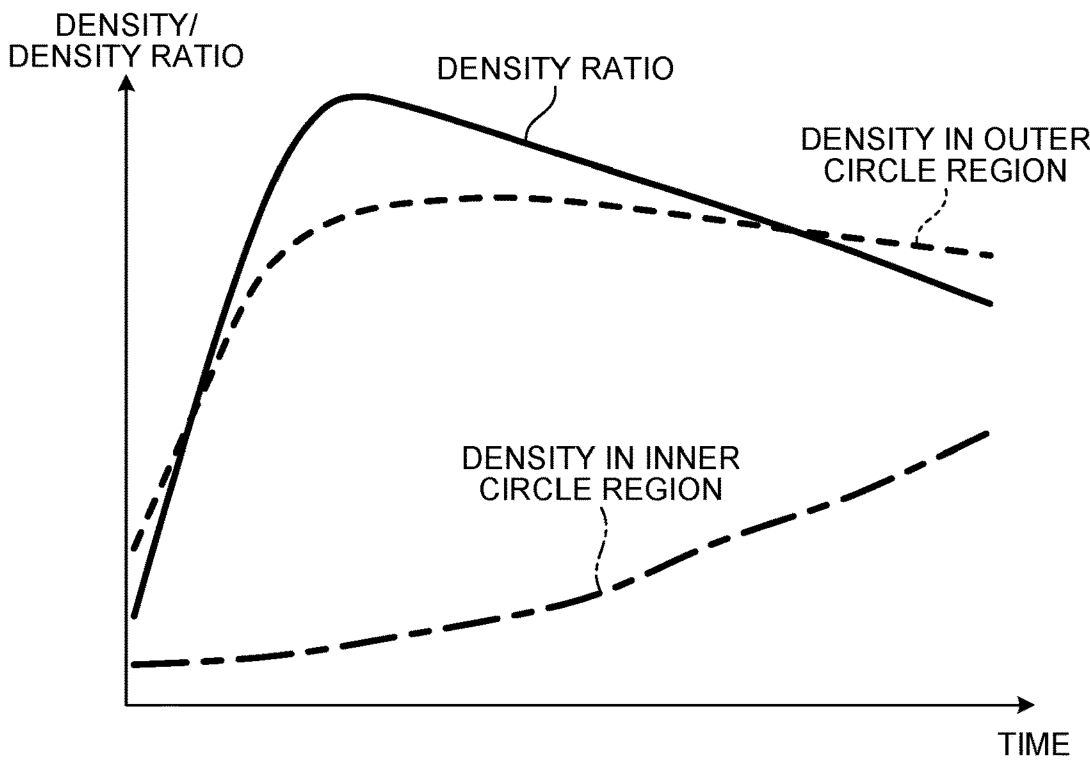
FIG. 9A and FIG. 9B are diagrams for explaining processing performed by a display control function according to the embodiment.
Figure 9B:
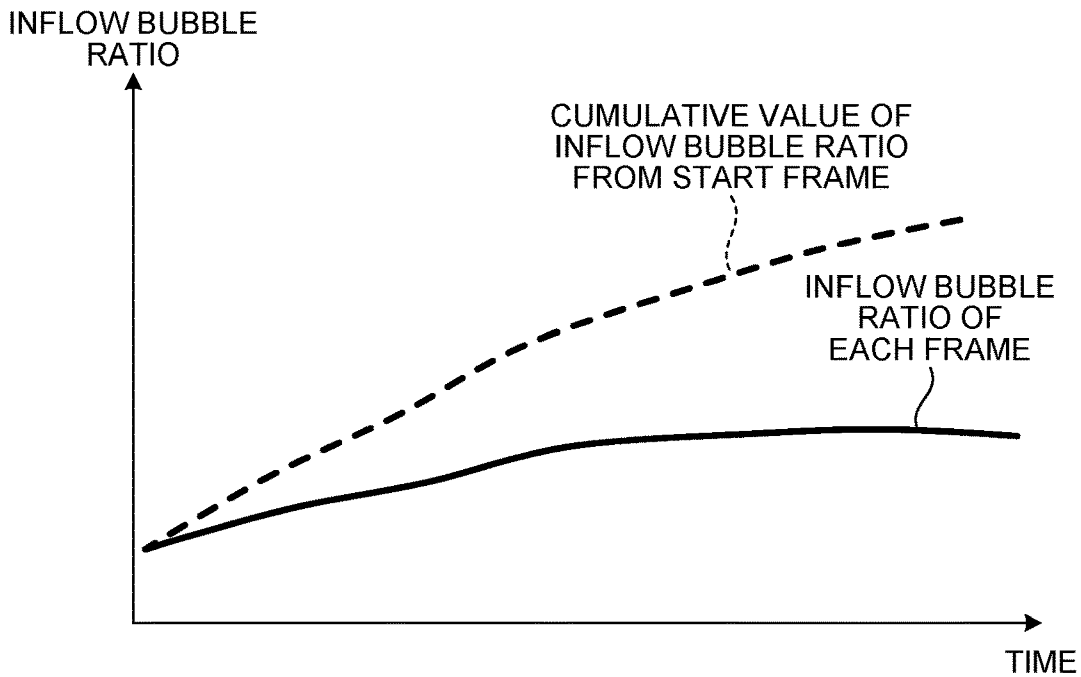

With reference to FIG. 9A and FIG. 9B, the following describes processing performed by the display control function 166 according to the embodiment. FIG. 9A and FIG. 9B are diagrams for explaining the processing performed by the display control function 166 according to the embodiment. In FIG. 9A and FIG. 9B, a horizontal axis corresponds to a time (elapsed time), and a vertical axis corresponds to a measurement result.

As illustrated in FIG. 9A, the display control function 166 displays a graph indicating temporal changes in the bubble density in the inner circle region, the bubble density in the outer circle region, and the bubble density ratio. For example, the display control function 166 generates and displays the graph of FIG. 9A by plotting the bubble density in the inner circle region, the bubble density in the outer circle region, and the bubble density ratio calculated for each frame in time series.

As illustrated in FIG. 9B, the display control function 166 displays a graph indicating temporal changes in the inflow bubble ratio of each frame and the cumulative value of the inflow bubble ratio from the start frame. For example, the display control function 166 generates and displays the graph of FIG. 9B by plotting the inflow bubble ratio calculated for each frame and the cumulative value of the inflow bubble ratio from the start frame in time series.

The content described in FIG. 9A and FIG. 9B is merely an example, and the embodiment is not limited thereto. For example, the display control function 166 can display, as a graph, an optional index value calculated by the first calculation function 163 and the second calculation function 165, not limited to the index value illustrated in FIG. 9A and FIG. 9B.

A display form is not limited to a graph. For example, the display control function 166 can display a numerical value of each index value as text data (a numeral). In this case, numerical values related to all frames can be displayed as text data, but it is preferable to display a numerical value related to a representative frame or a frame designated by the operator.

In this way, the ultrasonic diagnostic device 1 according to the embodiment performs the pieces of processing at step S101 to step S109 in FIG. 2. The processing procedure illustrated in FIG. 2 is not limited to the illustrated order, but can be optionally changed without causing contradiction in processing content. For example, the processing at step S106 may be performed after step S107 or step S108.

As described above, in the ultrasonic diagnostic device 1 according to the embodiment, the detection function 161 detects the contrast medium from the medical image. The setting function 162 then sets the first and the second region of interest in the medical image. The first calculation function 163 then calculates the density ratio between the density of the contrast medium included in the first region of interest and the density of the contrast medium included in the second region of interest. Due to this, the ultrasonic diagnostic device 1 can provide an index value based on distribution of the contrast medium.

For example, in a case of a malignant tumor, it is known that the contrast medium entered from the outside of the tumor reaches the vicinity of the center relatively rapidly. On the other hand, in a case of a benign tumor, it is known that, even when the contrast medium enters from the outside of the tumor, the contrast medium is once retained in the vicinity of an outer edge of the tumor, and reaches the vicinity of the center more slowly as compared with the malignant tumor. Thus, the ultrasonic diagnostic device 1 calculates the bubble density separately for the outer circle region including the outer edge of the tumor and the inner circle region including the center of the tumor, and calculates a ratio (bubble density ratio) therebetween. The ultrasonic diagnostic device 1 then presents, to the operator, the calculated bubble density in the outer circle region, bubble density in the inner circle region, and bubble density ratio. Due to this, the operator is enabled to easily discriminate between a benign tumor and a malignant tumor.

In the ultrasonic diagnostic device 1 according to the embodiment, the tracking function 164 calculates the motion vector of the contrast medium by tracking the position of the contrast medium in each of the medical images arranged in time series. The second calculation function 165 then calculates the inflow/outflow ratio of the contrast medium in the region of interest based on the motion vector. Due to this, the ultrasonic diagnostic device 1 can provide an index value based on distribution of the contrast medium.

For example, it is known that an inflow amount of blood flow for the malignant tumor is larger than that for the benign tumor, and an outflow amount of blood flow for the benign tumor is larger than that for the malignant tumor. Thus, the ultrasonic diagnostic device 1 calculates the inflow/outflow ratio to be presented to the operator. Due to this, the operator is enabled to easily discriminate between a benign tumor and a malignant tumor.

In the embodiment, described is a case in which the ultrasonic diagnostic device 1 includes both of the first calculation function 163 and the second calculation function 165, but the ultrasonic diagnostic device 1 may include only one of them. In a case in which the ultrasonic diagnostic device 1 includes only the first calculation function 163, the tracking function 164 is not necessarily included therein. In a case in which the ultrasonic diagnostic device 1 includes only the second calculation function 165, the setting function 162 may set at least one region of interest.

First Modification

In the embodiment described above, exemplified is a case of calculating the density and the density ratio in the predetermined time phase, but the embodiment is not limited thereto. For example, the first calculation function 163 may calculate the cumulative value or the average value in the predetermined section as the density and the density ratio.

For example, the first calculation function 163 calculates a cumulative density in the outer circle region in optional three frames by dividing the number of bubbles (cumulative value) detected in the optional three frames in the outer circle region (or the inner circle region) by an area of the outer circle region (or the inner circle region). The first calculation function 163 also calculates an average density in the outer circle region by dividing the cumulative density in the outer circle region in the three frames by the number of frames "3". Furthermore, the first calculation function 163 calculates the density ratio by taking a ratio between the outer circle region and the inner circle region with respect to the cumulative density or the average density.

That is, the first calculation function 163 can calculate a value in the predetermined time phase, or a cumulative value or an average value in the predetermined section as the density and the density ratio.

Second Modification

The first calculation function 163 can also calculate the cumulative value or the average value in the predetermined section described in the first modification while eliminating double-counting of an identical bubble.

For example, the first calculation function 163 calculates the cumulative density in the outer circle region in the optional three frames by dividing the number of bubbles identified with the identification information among the bubbles detected in the optional three frames in the outer circle region (or the inner circle region) by the area of the outer circle region (or the inner circle region). The first calculation function 163 also calculates the average density in the outer circle region by dividing the cumulative density in the outer circle region in the three frames by the number of frames "3". Furthermore, the first calculation function 163 calculates the density ratio by taking the ratio between the outer circle region and the inner circle region with respect to the cumulative density or the average density.

In this way, by counting the number of bubbles identified with the identification information, the first calculation function 163 can calculate the cumulative value or the average value in the predetermined section while eliminating double-counting of an identical bubble using the bubble ID.

In the second modification, the bubble ID output through the tracking processing for a bubble is used. Thus, it is preferable that the first calculation function 163 according to the second modification performs the processing after the tracking function 164 performs the tracking processing.

Other Embodiments

Various different embodiments may be applied in addition to the embodiment described above.

Medical Image Processing Device

For example, the above embodiment describes a case in which the disclosed technique is applied to the ultrasonic diagnostic device 1, but the embodiment is not limited thereto. For example, the disclosed technique may be applied to a medical image processing device 200. The medical image processing device 200 corresponds to, for example, a workstation, a Picture Archiving Communication System (PACS) viewer, and the like. The medical image processing device 200 is an example of an image processing device.

Figure 10:
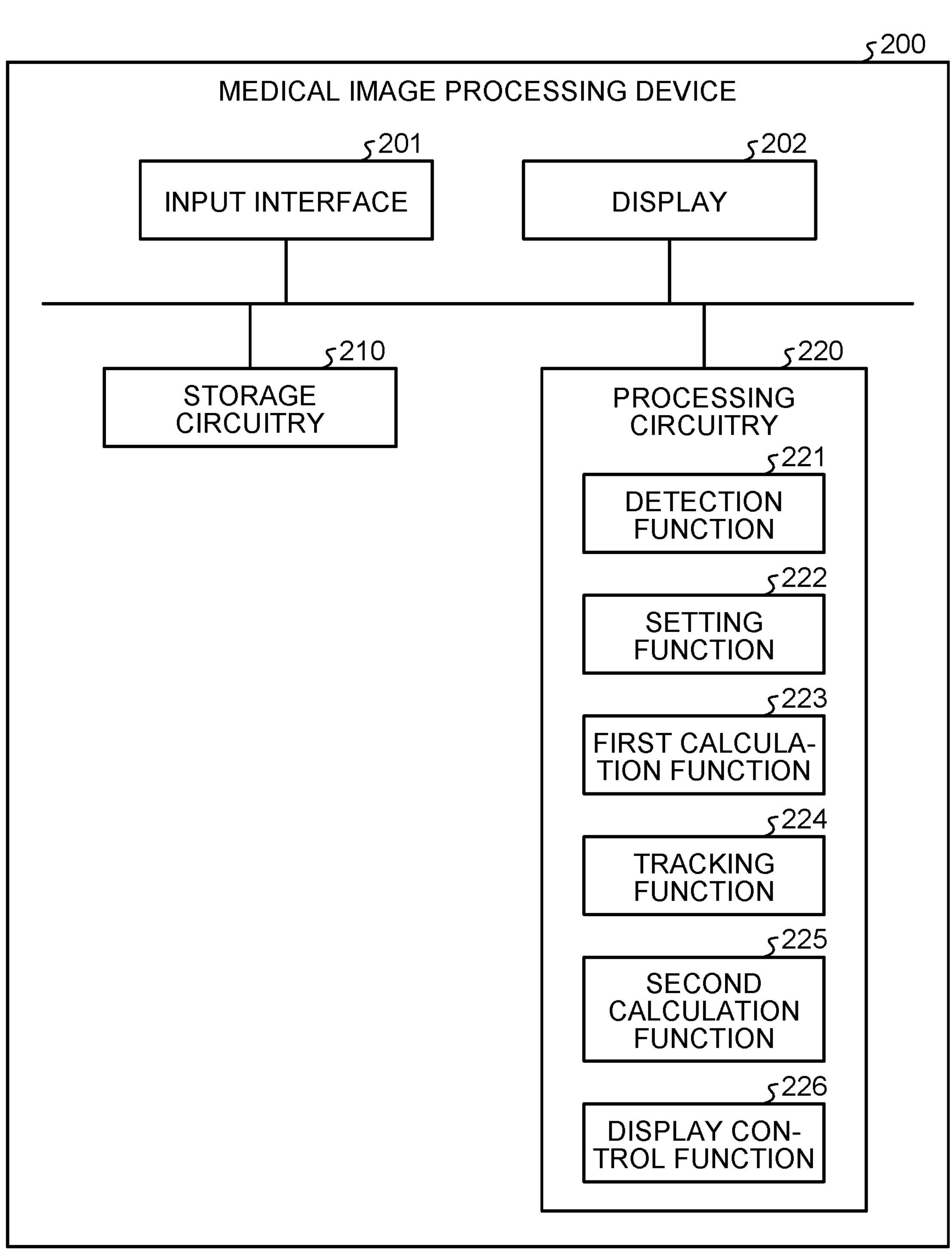
FIG. 10 is a block diagram illustrating a configuration example of a medical image processing device according to another embodiment.

FIG. 10 is a block diagram illustrating a configuration example of the medical image processing device 200 according to another embodiment. As illustrated in FIG. 10, the medical image processing device 200 includes an input interface 201, a display 202, storage circuitry 210, and processing circuitry 220. The input interface 201, the display 202, the storage circuitry 210, and the processing circuitry 220 are connected to each other in a communicable manner.

The input interface 201 is an input device for receiving various instructions and setting requests from the operator such as a mouse, a keyboard, and a touch panel. The display 202 is a display device for displaying a medical image, or displaying a GUI with which the operator inputs various setting requests using the input interface 201.

The storage circuitry 210 is, for example, Not AND (NAND) flash memory or a hard disk drive (HDD), and stores various computer programs for displaying medical image data or a GUI, and information used by the computer programs.

The processing circuitry 220 is an electronic appliance (processor) that controls the entire processing performed by the medical image processing device 200. The processing circuitry 220 executes a detection function 221, a setting function 222, a first calculation function 223, a tracking function 224, a second calculation function 225, and a display control function 226. Each of the detection function 221, the setting function 222, the first calculation function 223, the tracking function 224, the second calculation function 225, and the display control function 226 is, for example, recorded in the storage circuitry 210 in the form of a computer-executable program. The processing circuitry 220 reads out and executes the respective computer programs to implement functions (the detection function 221, the setting function 222, the first calculation function 223, the tracking function 224, the second calculation function 225, and the display control function 226) corresponding to the respective read-out computer programs.

The processing functions of the detection function 221, the setting function 222, the first calculation function 223, the tracking function 224, the second calculation function 225, and the display control function 226 are the same as the processing functions of the detection function 161, the setting function 162, the first calculation function 163, the tracking function 164, the second calculation function 165, and the display control function 166 illustrated in FIG. 1, so that the description thereof will be omitted.

Due to this, the medical image processing device 200 can provide an index value based on distribution of the contrast medium. The ultrasonic diagnostic device 1 described in the above embodiment corresponds to an ultrasonic diagnostic device including the medical image processing device 200.

The components of the devices illustrated in the drawings are merely conceptual, and it is not required that they are physically configured as illustrated necessarily. That is, specific configurations of distribution and integration of the devices are not limited to those illustrated in the drawings. All or part thereof can be configured by functionally or physically distributing/integrating in arbitrary units depending on various loads, usage states, and the like. Additionally, all or optional part of the processing functions executed by the respective devices may be implemented as a CPU and a computer program analyzed and executed by the CPU, or may be implemented as hardware using wired logic.

Among the pieces of processing described in the embodiments and the modifications, all or part of the pieces of processing described to be automatically performed can be manually performed, or all or part of the pieces of processing described to be manually performed can be automatically performed using a well-known method. Besides this, the processing procedures, the control procedures, the specific names, and the information including various pieces of data or parameters described herein or illustrated in the drawings can be optionally changed unless otherwise specifically noted.

The medical image processing method described in the embodiments and the modifications can be implemented by executing a medical image processing program prepared in advance by a computer such as a personal computer or a workstation. The medical image processing program can be distributed via a network such as the Internet. The medical image processing program can be recorded in a computer-readable non-transitory recording medium such as a hard disk, a flexible disk (FD), a CD-ROM, an MO, and a DVD, and can be executed by being read out from the recording medium by a computer.

In the embodiments and modifications described above, "in substantially real time" means to immediately perform each piece of processing every time each piece of data as a processing target is generated. For example, the processing of displaying an image in substantially real time is a concept not only including a case in which a time when the subject is imaged completely matches a time when the image is displayed, but also a case in which the image is displayed with a slight time lag depending on a time required for each piece of processing such as image processing.

A phrase of "image data" and a term of "image" described above in the embodiment are different from each other in a strict sense. That is, in the "image data", each pixel position is associated with a luminance value at each pixel position. The "image" is displayed on a display device such as a display such that a color corresponding to a luminance value at each pixel position is mapped to each pixel position. However, most of typical image processing techniques influence both of the "image data" and the "image", and rarely influence any one of them. Thus, unless otherwise specifically noted, the "image data" and the "image" may be written without being strictly distinguished from each other.

According to at least one of the embodiments described above, an index value based on distribution of the contrast medium can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing device, comprising:
processing circuitry configured to:
sequentially acquire ultrasound images of a subject, and detect, from each acquired ultrasound image, individual microbubbles included in a contrast medium administered to a subject,
calculate a density of microbubbles in a first region of interest (ROI) in each ultrasound image by dividing a number of detected microbubbles in the first ROI by an area of the first ROI,
calculate a density of microbubbles in a second ROI that is located inside the first ROI, and completely surrounded by the first ROI, by dividing a number of detected microbubbles in the second ROI by an area of the second ROI, and
output information, based on the plurality of sequentially acquired ultrasound images, that indicates temporal changes in the microbubble densities in the first and second ROIs and allows identification of which ROI has a higher or lower microbubble density over time.

2. The medical image processing device according to claim 1, wherein the processing circuitry is further configured to calculate, as the information, values of the density of microbubbles in the first ROI, the density of the microbubbles in the second ROI, and a density ratio between the density of microbubbles in the first ROI and the density of the microbubbles in the second ROI in a predetermined time phase, or a cumulative value or an average value of the values in a predetermined section.

3. The medical image processing device according to claim 2, wherein the processing circuitry is further configured to calculate the cumulative value or the average value in the predetermined section while eliminating double-counting of an identical bubble.

4. The medical image processing device according to claim 1, wherein the processing circuitry is further configured to:
calculate a motion vector of the microbubbles by tracking a position of the microbubbles in each of a plurality of ultrasound images arranged in time series, and
calculate an inflow/outflow ratio of the microbubbles in at least one of the first ROI and the second ROI based on the calculated motion vector.

5. The medical image processing device according to claim 4, wherein the processing circuitry is further configured to calculate, as the inflow/outflow ratio, at least one of:
a value obtained by dividing a number of inflow bubbles by a number of inflow/outflow bubbles, a value obtained by dividing a number of outflow bubbles by the number of inflow/outflow bubbles,
a value obtained by dividing the number of inflow bubbles by the number of outflow bubbles, and
a value obtained by dividing the number of outflow bubbles by the number of inflow bubbles.

6. The medical image processing device according to claim 4, wherein the processing circuitry is further configured to calculate, as the inflow/outflow ratio, a value in a predetermined time phase, or a cumulative value or an average value in a predetermined section.

7. The medical image processing device according to claim 6, wherein the processing circuitry is further configured to calculate the cumulative value or the average value in the predetermined section while eliminating double-counting of an identical bubble.

8. The medical image processing device according to claim 4, wherein the processing circuitry is further configured to display information indicating temporal changes in the inflow/outflow ratio.

9. The medical image processing device according to claim 1, wherein the medical image processing device is an ultrasonic diagnostic device.

10. The medical image processing device according to claim 1, wherein the first region of interest is an annular region.

11. A medical image processing device, comprising:

processing circuitry configured to:

sequentially acquire ultrasound images of a subject, detect, from the acquired ultrasound images, individual microbubbles of a contrast medium administered to the subject, set a region of interest in each ultrasound image, calculate a motion vector of the contrast medium by tracking a position of the contrast medium in each of the ultrasound images arranged in time series, calculate, based on the calculated motion vector, an angle representing a moving direction of the contrast medium with respect to a reference position for each contrast medium bubble within the region of interest, identify an inflow bubble and an outflow bubble among the contrast medium based on the calculated angle and a set angle range, and calculate an inflow/outflow ratio of the contrast medium in the region of interest based on a number of identified inflow bubbles and a number of identified outflow bubbles.

12. The medical image processing device according to claim 11, wherein the processing circuitry is further configured to calculate, as the inflow/outflow ratio, at least one of:

a value obtained by dividing a number of inflow bubbles by a number of inflow/outflow bubbles, a value obtained by dividing a number of outflow bubbles by the number of inflow/outflow bubbles, a value obtained by dividing the number of inflow bubbles by the number of outflow bubbles, and a value obtained by dividing the number of outflow bubbles by the number of inflow bubbles.

13. The medical image processing device according to claim 11, wherein the processing circuitry is further configured to calculate, as the inflow/outflow ratio, a value in a predetermined time phase, or a cumulative value or an average value in a predetermined section.

14. The medical image processing device according to claim 13, wherein the processing circuitry is further configured to calculate the cumulative value or the average value in the predetermined section while eliminating double-counting of an identical bubble.

15. The medical image processing device according to claim 11, wherein the processing circuitry is further configured to display information indicating temporal changes in the inflow/outflow ratio.

16. The medical image processing device according to claim 11, wherein the medical image processing device is an ultrasonic diagnostic device.

17. A computer program product having a non-transitory computer readable recording medium including programmed instructions, wherein the instructions, when executed by a computer, cause the computer to perform:

sequentially acquiring ultrasound images of a subject, and detecting, from each acquired ultrasound image, individual microbubbles included in a contrast medium administered to a subject;

calculating a density of microbubbles in a first region of interest (ROI) in each ultrasound image by dividing a number of detected microbubbles in the first ROI by an area of the first ROI, calculating a density of microbubbles in a second ROI that is located inside the first ROI and completely surrounded by the first ROI, by dividing a number of detected microbubbles in the second ROI by an area of the second ROI, and outputting information, based on the plurality of sequentially acquired ultrasound images, that indicates temporal changes in the microbubble densities in the first and second ROIs and allows identification of which ROI has a higher or lower microbubble density over time.

18. A computer program product having a non-transitory computer readable recording medium including programmed instructions, wherein the instructions, when executed by a computer, cause the computer to perform:

sequentially acquiring ultrasound images of a subject:

detecting, from the acquired ultrasound images, individual microbubbles of a contrast medium administered to the subject from a plurality of ultrasound images arranged in time series, the contrast medium including that includes an amount of microbubbles that do not overlap with each other;

setting a region of interest in each ultrasound image;

calculating a motion vector of the contrast medium by tracking a position of the contrast medium in each of the ultrasound images arranged in time series;

calculating, based on the calculated motion vector, an angle representing a moving direction of the contrast medium with respect to a reference position for each contrast medium bubble within the region of interest;

identifying an inflow bubble and an outflow bubble among the contrast medium based on the calculated angle and a set angle range; and calculating an inflow/outflow ratio of the contrast medium in the based on a number of identified inflow bubbles and a number of identified outflow bubbles.

* * * * *